US00PP34685P2

(12) United States Plant Patent
Wood

(10) Patent No.: US PP34,685 P2
(45) Date of Patent: Oct. 25, 2022

(54) ***THUJA* PLANT NAMED 'SMTOBM3'**

(50) Latin Name: *Thuja occidentalis*
Varietal Denomination: SMTOBM3

(71) Applicant: Spring Meadow Nursery, Inc, Grand Haven, MI (US)

(72) Inventor: Timothy D. Wood, Spring Lake, MI (US)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/540,984

(22) Filed: Dec. 2, 2021

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Anne Marie Grunberg
(74) *Attorney, Agent, or Firm* — Cassandra Bright

(57) ABSTRACT

A new and distinct variety of *Thuja* plant named 'SMTOBM3' is disclosed, characterized by a narrow, columnar plant habit and dense foliage. Plants have distinctive twisting to the branchlets and cold tolerance to USDA Zone 3. The new cultivar is a *Thuja*, suitable for ornamental garden purposes.

2 Drawing Sheets

Latin name of the genus and species: *Thuja occidentalis*.
Variety denomination: 'SMTOBM3'.

BACKGROUND OF THE INVENTION

The new cultivar, hereinafter referred to as 'SMTOBM3', was discovered as part of a breeding program at a commercial nursery in Grand Haven, Mich. The intention of the breeding program was to develop new *Thuja* varieties with novel plant habits and forms for commercial purposes. This new discovery is the result of an open-pollination of the seed parent *Thuja occidentalis* 'Brandon' (unpatented) with unidentified pollen parents conducted during 2003.

The new variety was first identified as an interesting new plant during 2007 at the same commercial nursery in Grand Haven, Mich. After identifying the new variety as a potentially interesting selection, the inventor first organized propagation of 'SMTOBM3' by softwood cuttings at the same commercial nursery during 2007. The inventor continued controlled testing and propagation, assessing stability of the unique characteristics of this variety. At least thirteen generations have been reproduced and have shown that the unique features of this cultivar are stable and reproduced true to type.

SUMMARY OF THE INVENTION

The cultivar 'SMTOBM3' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMTOBM3' These characteristics in combination distinguish 'SMTOBM3' as a new and distinct *Thuja* cultivar:

1. Narrow, columnar plant habit.
2. Dense foliage.

3. Uniquely twisted branchlets.
5. Cold tolerance to USDA Zone 3.

COMPARISON TO PARENT VARIETY

'SMTOBM3' is similar in most horticultural characteristics to the parent variety *Thuja occidentalis* 'Brandon'. Plants of the new cultivar 'SMTOBM3' however, differ in the following:

1. The new variety grows to 3 to 4 feet wide at reaching a height of 12 to 15 feet. The parent variety grows twice this wide(6 to 8 feet) at the same height.

COMMERCIAL COMPARISON

*Thuja* 'SMTOBM3' can be compared to the commercial variety *Thuja* 'ArtBoe', U.S. Plant Pat. No. 22,174. Plants are similar in most horticultural characteristics, however, plants of the new variety differ in the following:

1. Plant shape of 'SMTOBM3' is narrower and more columnar. Plants of this comparator are less narrow, with a flared base.
2. Branchlets of 'SMTOBM3' are more twisted than branchlets of this comparator.
3. Branchlets of 'SMTOBM3' are less fine and feathery than branchlets of this comparator.

BRIEF DESCRIPTION OF THE PHOTOGRAPHS

Figure 1:
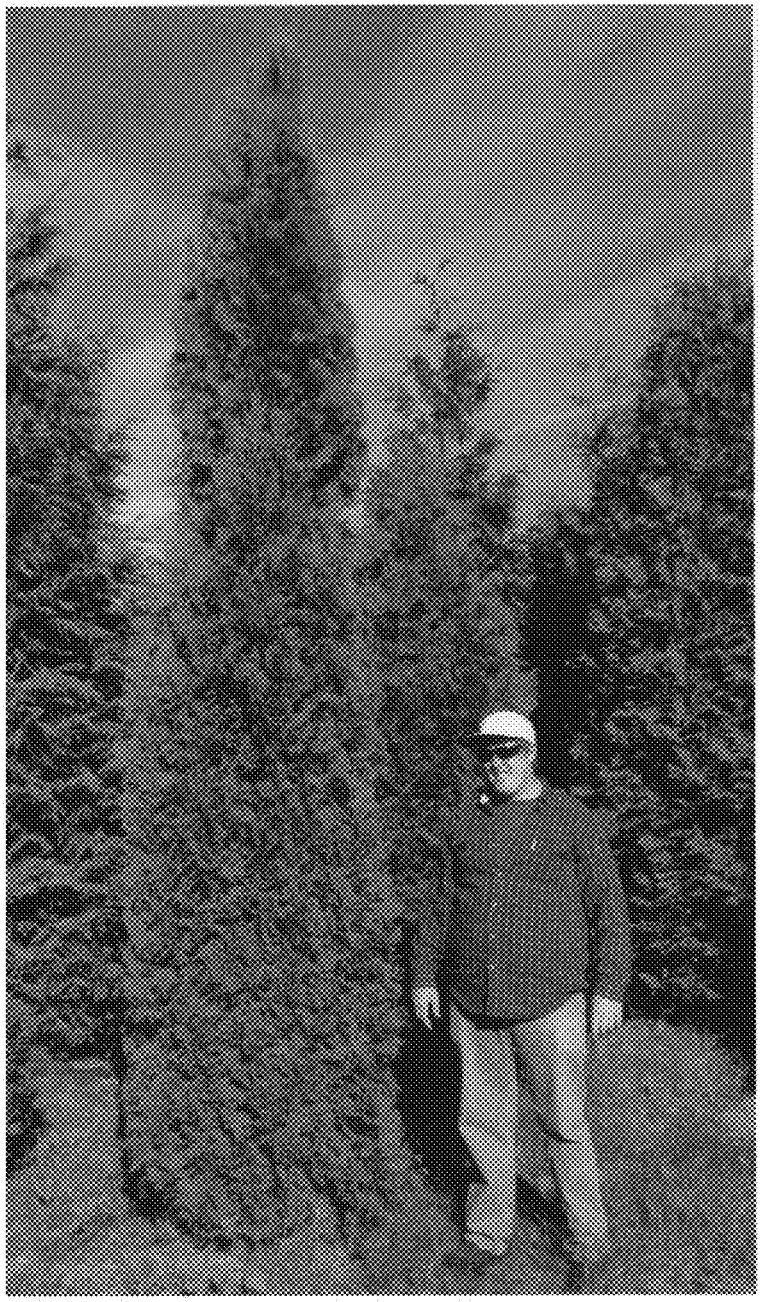

The accompanying photograph in FIG. 1 illustrates in full color a typical plant of 'SMTOBM3' grown outdoors in Grand Haven, Mich. The plants are approximately 8 years old, in the ground.

Figure 2:
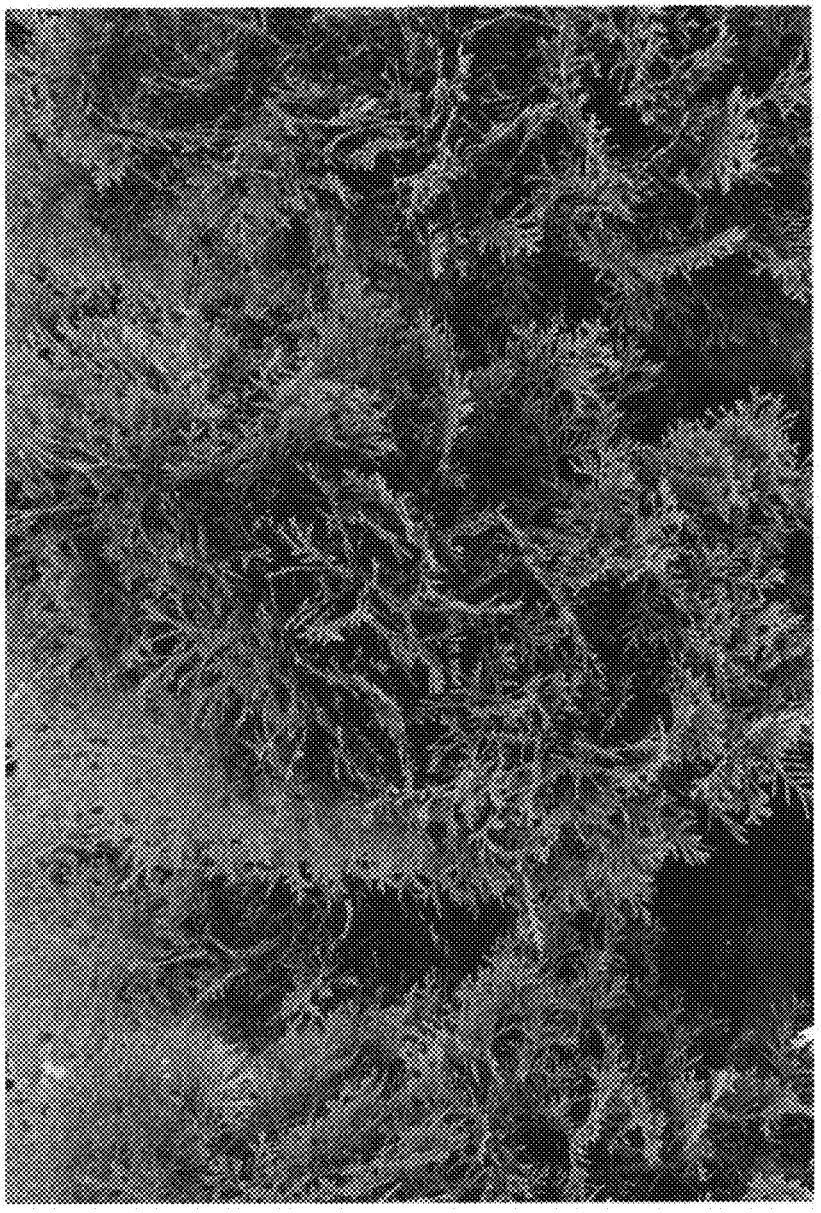

FIG. 2 illustrates a close up view of the branchlets of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'SMTOBM3' plants grown outdoors in Dayton, Oreg. Plants are approximately 2 to 3 years old, in a 3 gallon nursery container. Measurements and numerical values represent averages of typical plant types.

Botanical classification: *Thuja occidentalis* 'SMTOBM3'.

PROPAGATION

Time to rooting: About 45 days at approximately 18-27° C.

Root description: Moderately dense branching. Slightly woody, both fine and thick roots present. Colored white and tan, not accurately measured with the R.H.S. chart.

PLANT

Growth habit: Perennial evergreen tree with a columnar habit.

Height: 65 cm.

Plant spread: 31 cm.

Typical growth rate: Moderate.

Pinching required: No.

Branching characteristics: Upwards at acute angles.

Average number of lateral branches: About 5 to 8 major vertical branches.

Length of lateral branches: 49 to 60 cm.

Diameter of lateral branches: 5 mm.

Lateral branch shape in cross section: Oval.

Lateral branch texture: Rough, scaly.

Branch angle: About 15 degrees from center.

Lateral branch color: Greyed-Orange 174B with mature bark near Grey-Brown 199B tinted Greyed-Red 181D.

Lateral branch strength: Very strong, flexible.

Internode length: Average range 2.5 to 4.5 cm.

Main stem:

*Diameter*.—About 2.5 cm at 2 years.

*Length*.—About 28 cm at 2 years.

*Color*.—Near RHS Greyed-Orange 177A.

*Texture*.—Slightly scaly at 2 years.

FOLIAGE

Leaf:

*Arrangement*.—Alternate, overlapping scales.

*Shape*.—Scales.

*Average length*.—1 mm.

*Average width*.—1 mm.

*Apex*.—Acuminate.

*Base*.—Truncate.

*Margin*.—Entire.

*Texture of top surface*.—Smooth, waxy.

*Texture of bottom surface*.—Smooth, waxy.

*Color*.—Young foliage upper side: Yellow-green N145B. Young foliage under side: Yellow-green N145B. Mature foliage upper side: Green 137A. Mature foliage under side: Green 137A. Winter coloration: No noticeable change from mature foliage color.

*Venation*.—Indistinguishable from leaf blade.

*Leaf gland*.—Oblong, approximately 0.08 mm long and 0.05 mm long. Only visible under magnification. Colored near Yellow-Green 145C.

*Fragrance*.—None.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 3 through 8.

What is claimed is:

1. A new and distinct cultivar of *Thuja* plant named 'SMTOBM3' as herein illustrated and described.

* * * * *